(12) United States Patent
Lin

(10) Patent No.: US 6,783,235 B1
(45) Date of Patent: Aug. 31, 2004

(54) FOG-FREE PROTECTIVE GLASSES

(75) Inventor: Titan Lin, Taipei (TW)

(73) Assignee: Gazelle Corporation, Taipei (TW)

( * ) Notice: Subject to any disclaimer, the term of this patent is extended or adjusted under 35 U.S.C. 154(b) by 0 days.

(21) Appl. No.: 10/760,417

(22) Filed: Jan. 21, 2004

(51) Int. Cl.[7] .............................................. G02C 11/08
(52) U.S. Cl. ................................. 351/62; 2/435; 2/436; 2/437
(58) Field of Search .......................... 351/62, 41, 158, 351/83, 84, 85; 2/435, 436, 437, 426

(56) References Cited

U.S. PATENT DOCUMENTS

| | | | | |
|---|---|---|---|---|
| 5,610,668 A | * | 3/1997 | Mage | 351/62 |
| 5,638,145 A | * | 6/1997 | Jannard et al. | 351/62 |
| 5,711,035 A | * | 1/1998 | Haslbeck | 2/436 |
| 6,050,684 A | * | 4/2000 | Mage | 351/62 |
| 6,233,342 B1 | * | 5/2001 | Fernandez | 381/62 |

\* cited by examiner

*Primary Examiner*—Hung Xuan Dang
(74) *Attorney, Agent, or Firm*—Rosenberg, Klein & Lee

(57) ABSTRACT

A pair of fog-free protective glasses has a frame and a lens. The frame has an embedded portion and a pair of temples pivotally connecting to two ends of the embedded portion. The embedded portion has upper and lower embedded plates to define an embedded groove therebetween, and two sides of the embedded portion are respectively formed with at least one guiding structure. Each guiding structure has at least one drainage hole. The lens is embedded in the embedded groove of the frame, and is respectively formed with a guiding portion. A leading airflow is thus produced from the guiding portion through the drainage hole for reducing fog formation on the lens.

12 Claims, 6 Drawing Sheets

FOG-FREE PROTECTIVE GLASSES

BACKGROUND OF THE INVENTION

1. Field of the Invention

The present invention relates to fog-free protective glasses, and particularly to a glasses structure with an airflow function for heat convection, which, especially when going forward, can promote airflow circulation for preventing fog from appearing on the lenses thereof and improving the eyesight of the user.

2. Description of the Prior Art

Conventional glasses provide a wearer with benefits in addition to clear eyesight in various conditions. However, the glasses of the prior art easily fog over, especially when a wearer perspires after sports or works. This is inconvenient, uncomfortable and even dangerous for the wearer. Contact lenses provide clear vision without fog-prone lenses, but cannot provide a windbreak or sunscreen like glasses do. There is presently, and there has always been, a consistent problem regarding the fogging of lenses of eyeglasses.

SUMMARY OF THE INVENTION

An object of the present invention is to provide fog-free protective glasses, and particularly to a glasses structure having an airflow function for heat convection and preventing fog from condensing on lenses thereof.

In order to achieve the above object, the present invention according to one aspect thereof provides fog-free protective glasses comprising a frame and a lens. The frame has an embedded portion and a pair of temples pivotally connecting to two ends of the embedded portion. The embedded portion has upper and lower embedded plates to define an embedded groove therebetween, and two sides of the embedded portion are respectively formed with at least one guiding structure. Each guiding structure has at least one drainage hole therein. The lens is embedded in the embedded groove of the frame, and respectively forms a guiding portion. A leading airflow is thereby provided from the guiding portion through the drainage hole for reducing fog formation on the lens.

BRIEF DESCRIPTION OF THE DRAWINGS

The various objects and advantages of the present invention will be more readily understood from the following detailed description when read in conjunction with the appended drawing, in which.

DESCRIPTION OF THE PREFERRED EMBODIMENT

Figure 1:
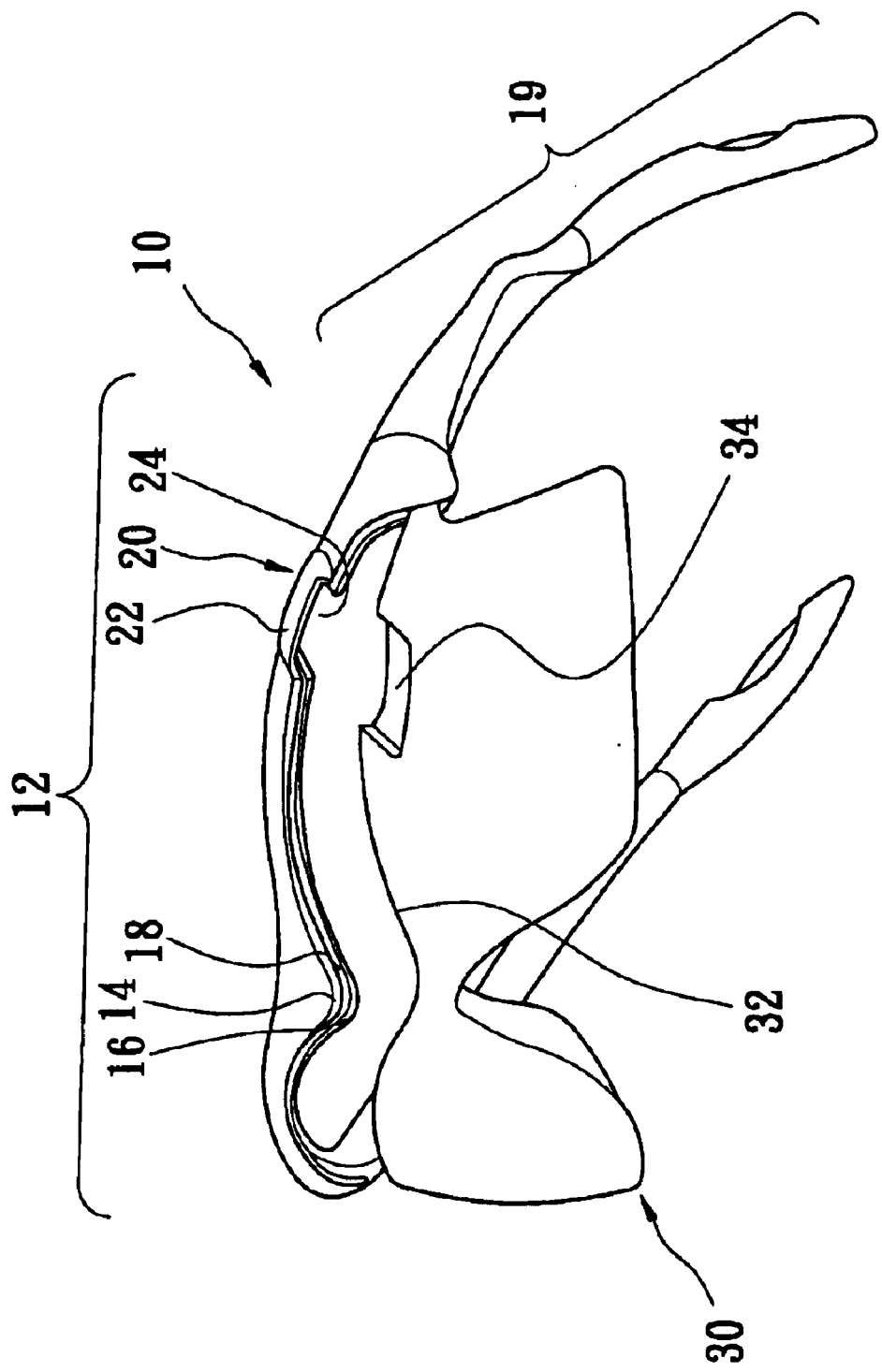
FIG. 1 is a perspective exploded view of the fog-free protective glasses according to the present invention.

Referring to FIG. 1, which is a perspective exploded view of the fog-free protective glasses according to the present invention, the present embodiment features single-rim glasses, but also can apply to surrounding rim glasses. A pair of fog-free protective glasses 10 comprises a frame 10 and a lens 30 embedded in the frame 10.

The frame 10 has an embedded portion 12 and a pair of temples 19, which are pivotally connecting to two ends of the embedded portion 12. The embedded portion 12 has upper and lower embedded plates 14, 16 to define an embedded groove 18 therebetween. Two sides of the embedded portion 12 respectively form at least one guiding structure 20. Each guiding structure 20 has an arched gathering plate 22 concaving inwardly from the upper embedded plate 14 and a drainage hole 24 is formed in the lower embedded plate 16 and under the gathering plate 22. The drainage hole 24 can be concaved upwardly from an edge of the lower embedded plate 16 or a through hole formed on the lower embedded plate 16, but the guiding effect of the former one is better than the latter one.

Figure 2:
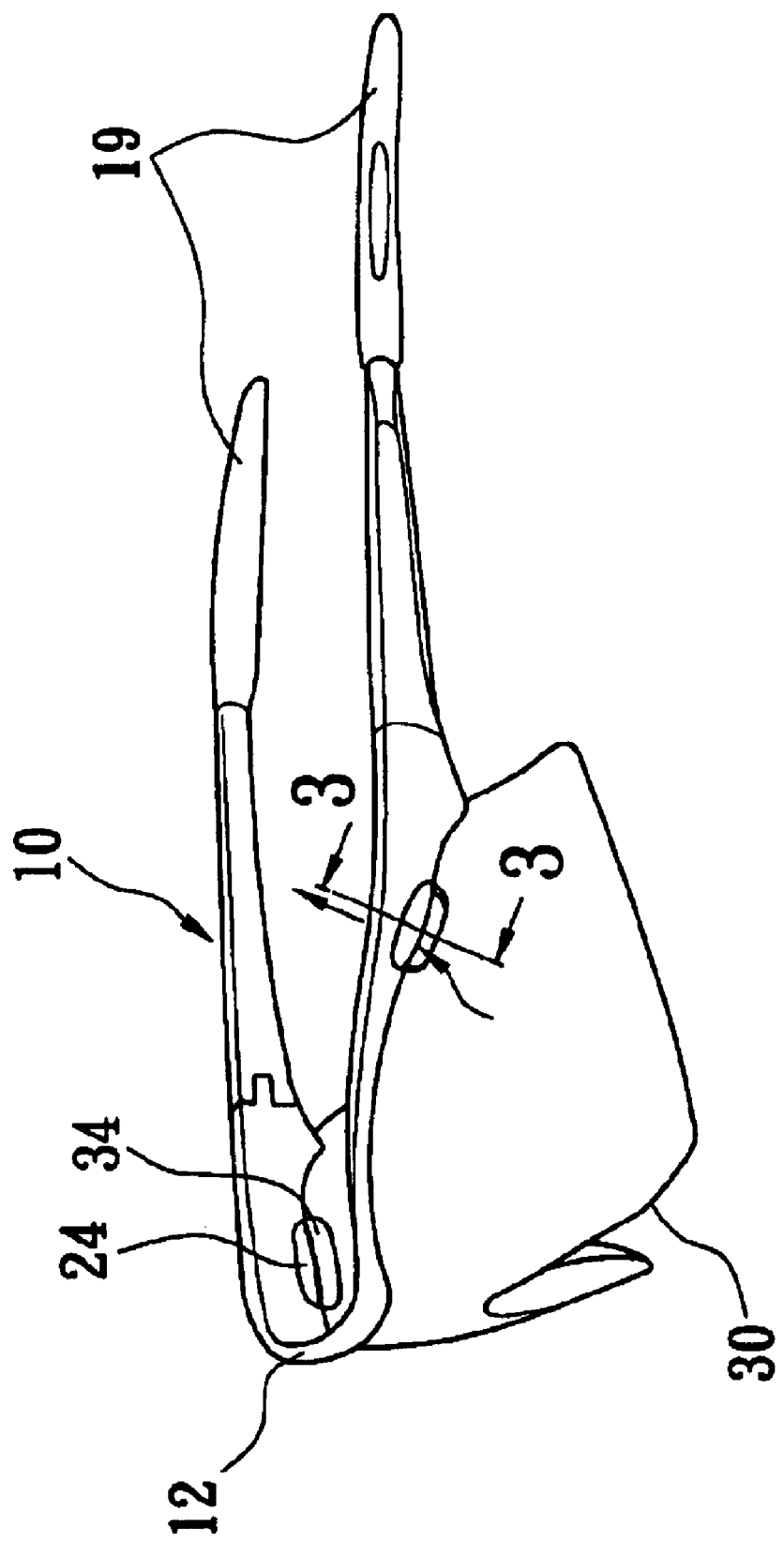
FIG. 2 is a perspective assembled view of the fog-free protective glasses according to the present invention.

The lens 30 is embedded in the embedded groove 18 of the frame 10 by an upper edge 32 thereof. Two sides of the lens 30 respectively form a concave guiding portion 34 corresponding to the guiding structure 20. Referring to FIG. 2, which is a perspective assembled view of the fog-free protective glasses according to the present invention, the glasses 10 can produce a guiding airflow from the guiding portion 34 of the lenses 30 through the drainage hole 24 of the guiding structure 20. Especially when the glasses-wearer goes forward, the guiding airflow can lead hot mist of the glasses-wearer to exhaust upwardly and reduce fog formation on the lens 30.

Figure 3A:
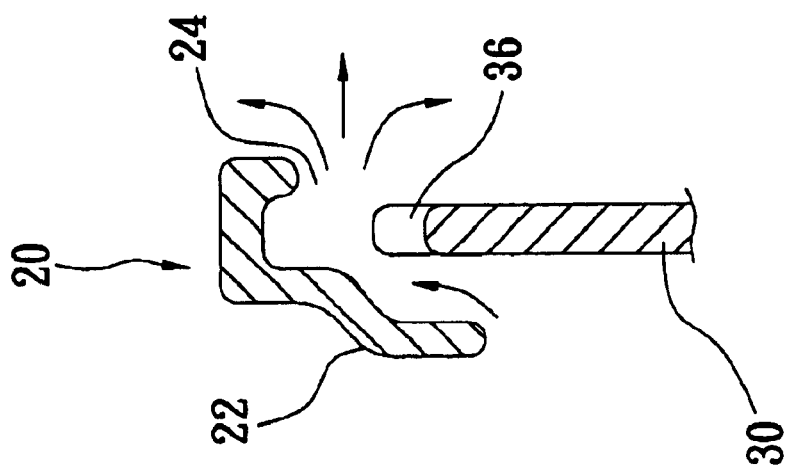
FIG. 3A is a first embodiment of the present invention along cross-sectional line 3—3 in FIG. 2.
Figure 3B:
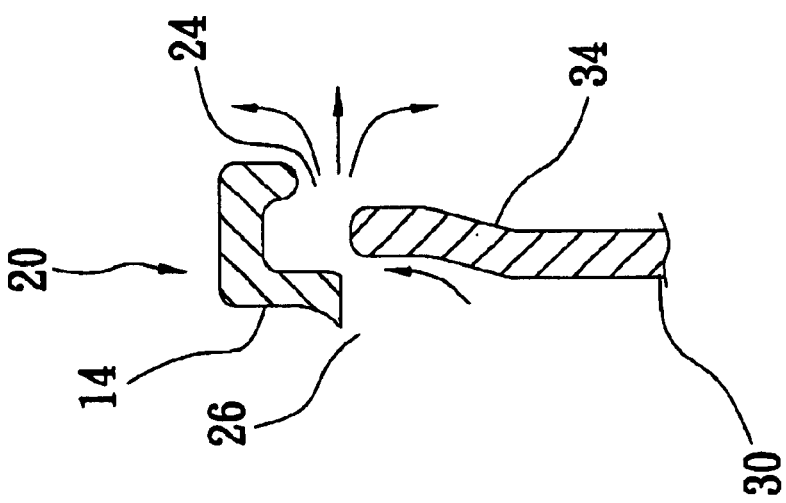
FIG. 3B is a second embodiment of the present invention along cross-sectional line 3—3 in FIG. 2.
Figure 3C:
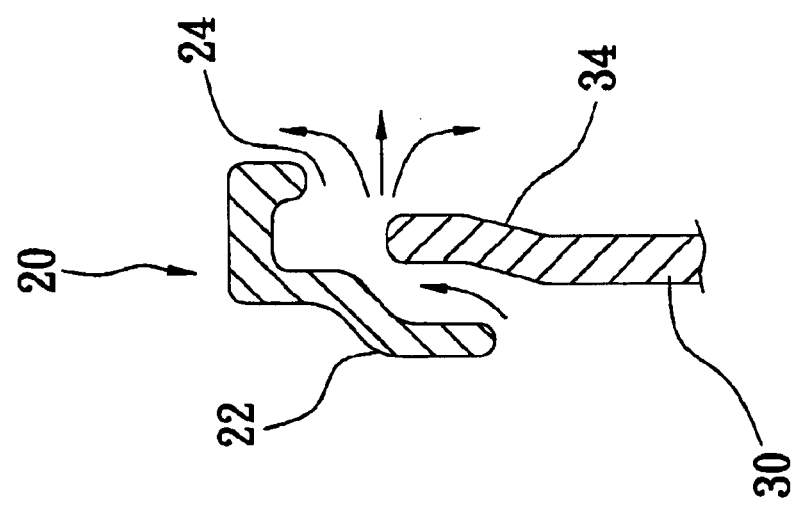
FIG. 3C is a third embodiment of the present invention along cross-sectional line 3—3 in FIG. 2.

Referring to FIGS. 3A to 3C, which are different embodiments of the present invention along cross-sectional line 3—3 in FIG. 2, the guiding structure 20 of the embedded portion 12 has a larger radian than that of the guiding portion 34 of the lens 30. When the lens 30 is embedded in the embedded portion 12, the upper edge 32 of the lens 30 does not contact a bottom of the embedded groove 18 and is thus formed with an air circulating space. The lens 30 embedded in the embedded portion 12 is centered on two sides and middle portion thereof, and therefore it does not affect the embedding stability.

Referring to FIG. 3A, which illustrates the first embodiment, the guiding structure 20 is formed with an arched gathering plate 22 on the upper embedded plate 14 and a drainage hole 24 formed in the lower embedded plate 16. The lens 30 is formed with a concave sheet-like guiding portion 34.

Referring to FIG. 3B, which illustrates the second embodiment, the guiding structure 20 is formed with an inletting hole 26 in the upper embedded plate 14 and a drainage hole 24 formed on the lower embedded plate 16. The lens 30 is formed with a concave sheet-like guiding portion 34.

Referring to FIG. 3C, which illustrates the third embodiment, the guiding structure 20 is formed with an arched gathering plate 22 on the upper embedded plate 14 and a drainage hole 24 formed on the lower embedded plate 16. The guiding portion 34 of the lens 30 is an excavated notch 36.

According to the mentioned embodiments of the present invention, the structure of the present invention has reverse replacement; that is to say, in FIG. 3A, the guiding structure 20 and the guiding portion 34 of the lens 30 can be replaced in reverse. The gathering plate 22 can be bent inwardly from the lower embedded plate 16. The drainage hole 24 can be formed on the upper embedded plate 14, and the guiding portion 34 of the lens 30 protrudes outwardly. Likewise, the same can be replace in reverse in FIGS. 3B and 3C. When the structure is replaced, because the lens of the glasses is usually arched and inclined inwardly, the direction of the airflow is guided downward and inwardly along the inner surface of the lens to blow to the periphery of the wearer's eyes and removes hot air for avoiding fog.

Figure 4:
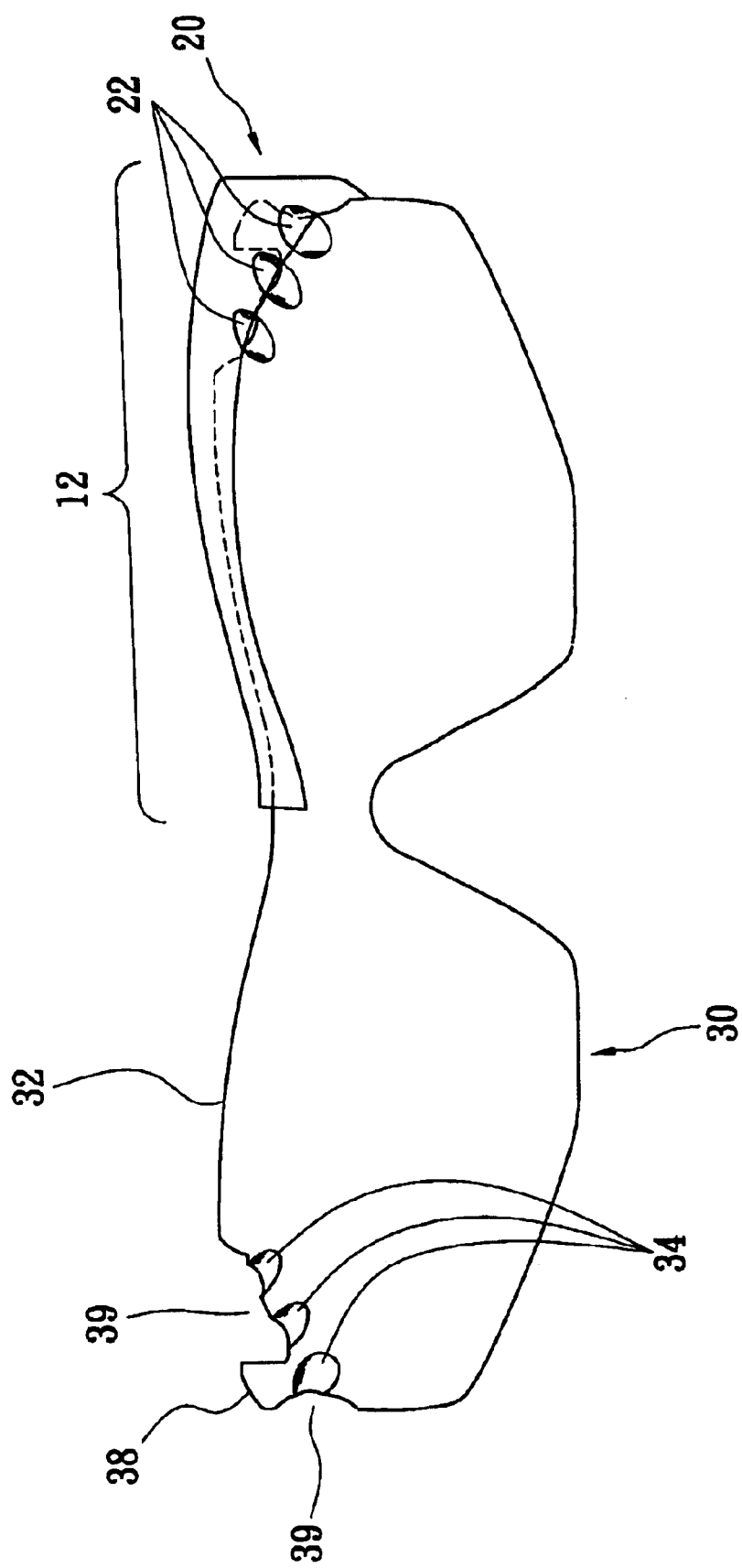
FIG. 4 is the best embodiment of the present invention with parts of the frame removed.

Referring. to FIG. 4, which is the best embodiment of the present invention with parts of the frame removed, the frame 12 is formed with three guiding structures 22 on left and right sides, respectively. The lens 30 is formed with three guiding portion 34 on left and right sides, respectively. The upper edges of the lens 30 further respectively comprises two convex corners 38 protruding upwardly on two sides thereof respectively for being embedded in the frame 12. Each convex corner 38 is formed with two concave cutouts 39 on two sides thereof. The bottom edges of the cutouts 39 are aligned with the edges of the frame 12. The guiding portions 34 are formed along the bottom edges of the cutouts 39 and are sheet-like concaved inwardly.

The present invention emphasizes that the lens of the glasses has a heat-convective structure to influence air flow for blowing hot air and preventing fog. Therefore the invention does not limit the style of the glasses to the above-mentioned illustration; the present invention can apply to rim-less glasses with decorative beams for producing the same function, or apply to surrounding rim glasses with the same structure for producing the same function.

Figure 5:
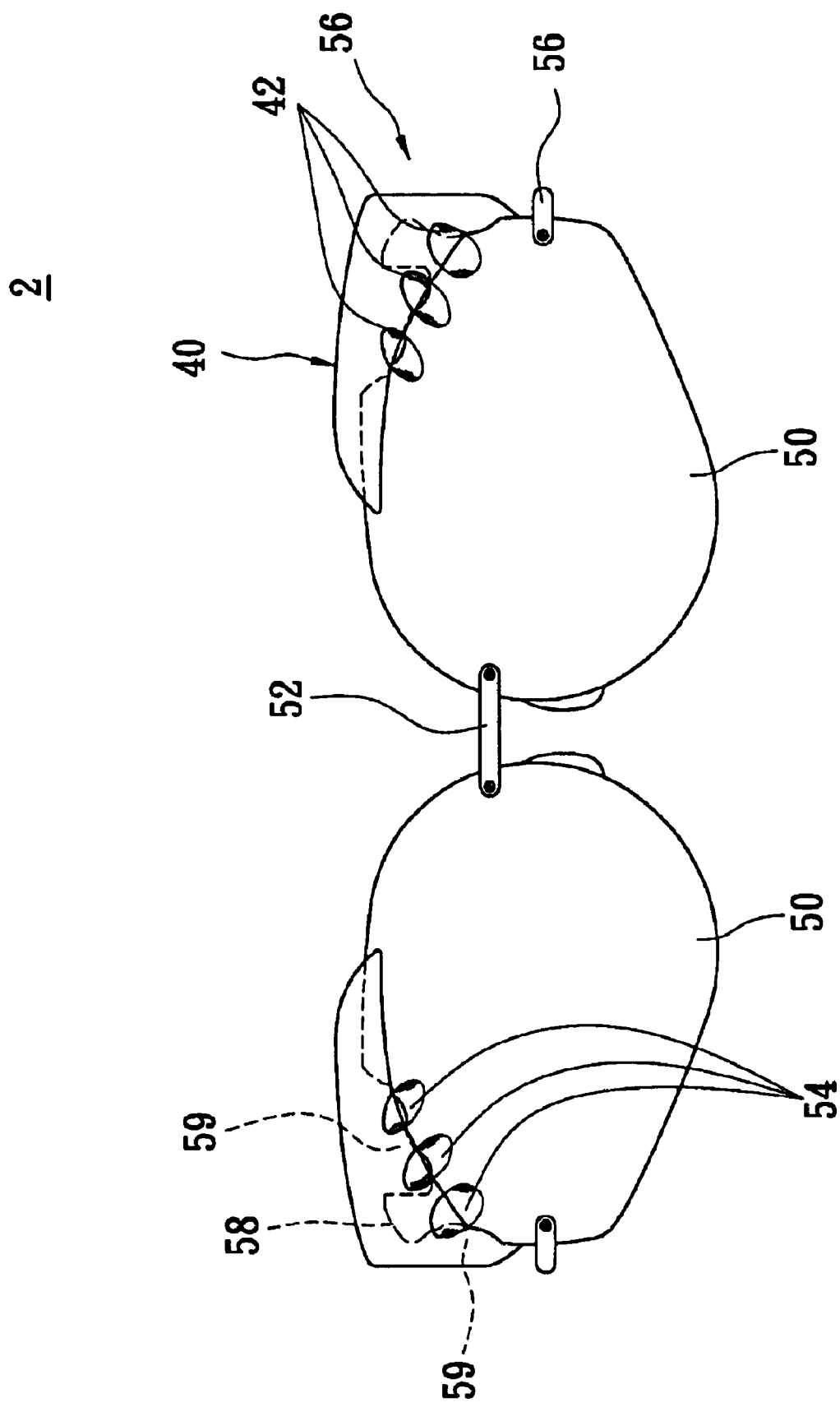
FIG. 5 is a front view of the present invention applying to rimless glasses.

Referring to FIG. 5, which is a front view of the present invention applying to rim-less glasses, the rimless glasses 2 has a pair of lenses 50, a bridge 52 connecting the pair of lenses 50, and a pair of temples 56 mounted on two ends of the pair lenses 50. Each lens 50 has a decorative beam 40 mounted thereon. The decorative beam 40, as in the above-mentioned frame, has upper and lower embedded plates for being embedded in the lenses 50. Each decorative beam 40 has an embedded portion that is formed with a guiding structure. The guiding structure is formed with at least one gathering plate 42 protruding outwardly from the upper embedded plate, and a corresponding drainage hole formed on the lower embedded plate. Each of the lenses 50 is formed with a concave guiding portion 54 corresponding to the gathering plate 42. The material of the decorative beam 40 is not limit to hard or soft, and even includes a design for greater aesthetic appeal. The lenses 50 further comprise a convex corner 58 and two cutouts 59 that are formed on two sides of the convex corner 58.

Figure 6:
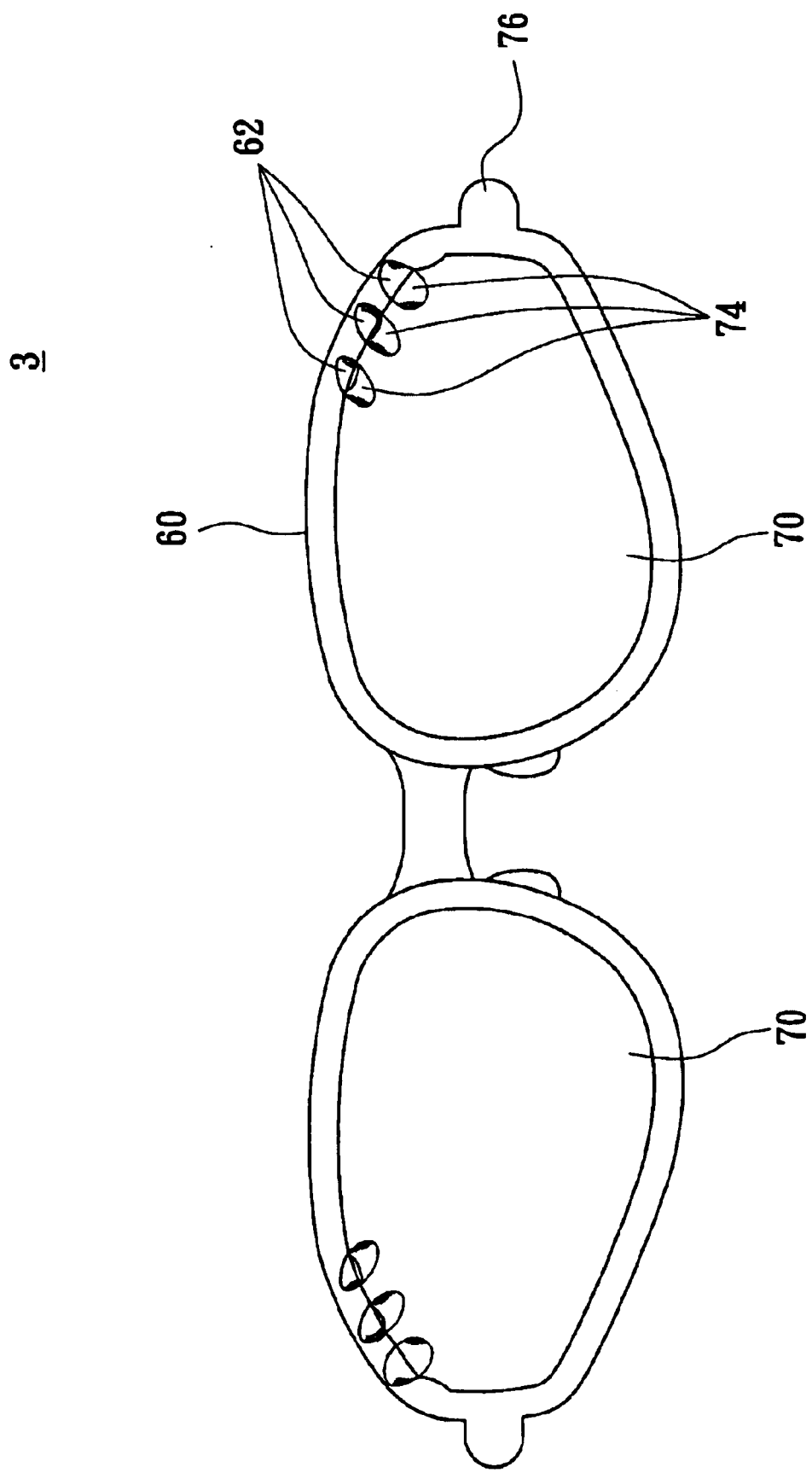
FIG. 6 is a front view of the present invention applied to surrounding rim glasses.

Referring to FIG. 6, which is a front view of the present invention applied to surrounding rim glasses, a pair of surrounding rim glasses 3 has a frame 60, a pair of lenses 50 fixed on the frame 60, and a pair of the temples 76 respectively mounted on two ends of the glasses 3. The frame 60 as the above-mentioned frame also has upper and lower embedded plates for being embedded on the lenses 50, and a guiding structure formed on two sides thereof, respectively. The guiding structure has at least one gathering plate 62 on the upper embedded plate and a drainage hole formed in the lower embedded plate. The lenses 70 have a concave guiding portion 74 formed thereon corresponding to the gathering plate 62. The plastic material of the frame 60 is better for molding. The two mentioned embodiments can also be modified to the forms illustrated in the FIGS. 3A to 3C.

To sum up, the advantages and functions of the present invention are as follows:

1. The glasses structure can produce airflow, especially when going forward, and can exhaust the hot mist from the wearer quickly for reducing fog and comfortable wear.

2. By the guiding airflow exhausting hot mist, the eyes of the wearer are more comfortable.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A fog-free protective glasses comprising:
   a frame having an embedded portion and a pair of temples pivotally connecting to two ends of the embedded portion, the embedded portion having upper and lower embedded plates to define a embedded groove therebetween, and two sides of the embedded portion respectively formed with at least one guiding structure, each guiding structure having at least one drainage hole; and
   a lens embedded in the embedded groove of the frame, and respectively forming a guiding portion, thereby producing a leading airflow from the guiding portion through the drainage hole for reducing fog forming on the lens.

2. The fog-free protective glasses as in claim 1, wherein the drainage hole of the guiding structure is formed on the lower embedded plate, and the guiding portion of the lenses is inwardly concave.

3. The fog-free protective glasses as in claim 2, wherein the guiding structure further comprises an arched gathering plate protruding outwardly from the upper embedded plate.

4. The fog-free protective glasses as in claim 1, wherein the drainage hole of the guiding structure is formed in the upper embedded plate, and the guiding portion of the lens protrudes inwardly.

5. The fog-free protective glasses as in claim 4, wherein the guiding structure further comprises an arched gathering plate concave inwardly from the lower embedded plate.

6. The fog-free protective glasses as in claim 1, wherein the guiding structure has a larger radian than that of the guiding portion of the lens.

7. The fog-free protective glasses as in claim 1, wherein the guiding portion of the lens is an excavated notch.

8. The fog-free protective glasses as in claim 1, wherein the upper edges of the lens respectively further comprises two convex corners protruding upwardly and respectively on two sides thereof for being embedded in the frame, each convex corner is formed with two concaved cutouts at two sides thereof, bottom edges of the cutouts are aligned the edges of the frame, and the guiding portion are formed along the bottom edges of the cutouts.

9. The fog-free protective glasses as in claim 1, wherein the frame is a single rim or a surrounding rim type.

10. A fog-free protective glasses, comprising:
    a pair of lenses connected via a bridge;
    a pair of temples respectively mounted on two outer sides of the pair lenses; and
    a pair of decorative beams respectively embedded in the pair lenses and forming a guiding structure, each guiding structure having at least one drainage hole formed therein, wherein the pair of lenses is respectively formed with a guiding portion on an upper edge thereof corresponding to the guiding structure, thereby producing a leading airflow from the guiding portion through the drainage hole for reducing fog formation on the lenses.

11. The fog-free protective glasses as in claim 10, wherein the pair decorative beams respectively have upper and lower embedded plates, the drainage hole is formed in the lower embedded plate, and the guiding portion of the lenses are concave in shape.

12. The fog-free protective glasses as in claim 11, wherein each upper embedded plate further comprises a gathering plate corresponding to the drainage hole.

* * * * *